United States Patent [19]
Hagiwara et al.

[11] Patent Number: 5,149,982
[45] Date of Patent: Sep. 22, 1992

[54] FOREIGN PARTICLE INSPECTION APPARATUS

[75] Inventors: Tsuneyuki Hagiwara, Tokyo; Fuminori Hayano, Yokohama, both of Japan

[73] Assignee: Nikon Corporation, Tokyo, Japan

[21] Appl. No.: 825,811

[22] Filed: Jan. 21, 1992

Related U.S. Application Data

[63] Continuation of Ser. No. 694,083, May 1, 1991, abandoned.

[30] Foreign Application Priority Data

May 7, 1990 [JP] Japan .................................. 2-117384

[51] Int. Cl.$^5$ ............................................. G01N 21/86
[52] U.S. Cl. ................................. 250/571; 356/239
[58] Field of Search .............. 356/239, 237, 430, 382, 356/240; 250/571, 572, 563, 271, 223 B

[56] References Cited

U.S. PATENT DOCUMENTS

| | | | |
|---|---|---|---|
| 4,249,075 | 2/1981 | Lovalenti | 356/240 |
| 4,468,120 | 8/1984 | Tanimoto et al. | 356/237 |
| 4,568,835 | 2/1986 | Imamura et al. | 250/572 |
| 4,790,662 | 12/1988 | Bischkopf et al. | 356/240 |
| 4,966,457 | 10/1990 | Hayano et al. | 250/572 |
| 5,032,732 | 7/1991 | Orazio, Jr. et al. | 250/572 |

*Primary Examiner*—David C. Nelms
*Assistant Examiner*—T. Davenport
*Attorney, Agent, or Firm*—Shapiro and Shapiro

[57] ABSTRACT

In a foreign particle inspection apparatus for detecting foreign particles present on a transparent object, a light beam is applied obliquely to one surface of the object, and the object and the light beam are moved relatively to scan an area of the surface. A photoelectric converter has a light receiving surface disposed to oppose the surface of the object and at least one end of the object. The converter receives scattered light from the foreign particles incident on the light receiving surface and outputs an electrical signal. A light intercepting member is disposed to intercept light propagated in the object from the scanning area toward the end of the object, that would otherwise be transmitted through the end of the object and travel externally of the object to the light receiving surface.

11 Claims, 5 Drawing Sheets

FOREIGN PARTICLE INSPECTION APPARATUS

This is a continuation of application Ser. No. 694,083, filed May 1, 1991, now abandoned.

BACKGROUND OF THE INVENTION

1. Field of the Invention

This invention relates to an optical type surface defect inspection apparatus for a transparent substrate such as glass, and particularly to a foreign particle inspection apparatus for the surface of a mask such as a reticle used in the semiconductor manufacturing process.

2. Related Background Art

U.S. Pat. No. 4,468,120 discloses an apparatus of this kind. In this prior-art apparatus, a light beam such as a laser beam emitted from a light source is swept by a scanner such as a vibratory mirror and enters a scanning lens. The light beam is applied as spotlight L onto the surface of a reticle by the scanning lens, and scans any given range. With the scanning direction of this spotlight L as the X-axis, the reticle is moved in the direction of the Y-axis substantially orthogonal to the X-axis, whereby the whole surface of the reticle can be scanned.

If there is any defect such as a foreign particle on the surface of the reticle at this time, scattered light is created by the spotlight L being applied to the foreign particle and is photoelectrically detected by a plurality of light receiving elements. Now, such scattered light is created not only from the foreign particle, but also as pattern scattered light or diffracted light from the edge of a circuit pattern depicted on the reticle. Incidentally, the pattern scattered light or the diffracted light has high directionality and can be distinguished from foreign particle scattered light of low directionality.

However, when such pattern scattered light or diffracted light enters the light receiving elements, it will be detected as scattered light from the foreign particle and accurate particle detection will become impossible. So, the plurality of light receiving elements are disposed so as to receive scattered light or diffracted light from different directions (in other words, so that all of the plurality of light receiving elements may not receive pattern scattered light or diffracted light of high directionality at one time). Accordingly, it can be judged that if scattered light enters all of the plurality of light receiving elements, this scattered light is that from the foreign particle and if there is any one of the plurality of light receiving elements which scattered light or diffracted light does not enter, this scattered light or diffracted light is that from the edge of the pattern.

These light receiving elements are disposed at an angle far from the direction in which pattern diffracted light of low order is created in order to make it difficult to receive low-order pattern diffracted light of high luminance. This also is a disposition which makes it difficult to receive pattern scattered light of high luminance.

Further, it is also known to use an apparatus as disclosed in U.S. Pat. No. 4,568,835 in order to prevent light (stray light) created on and in a reticle when light is applied to the reticle from entering light receiving elements. In this apparatus of a construction wherein a light beam emitted from a laser source is obliquely applied to the surface of a reticle and the light beam and the reticle are scanned relative to each other and scattered light from a foreign particle on the surface of the reticle is received by a light receiving device disposed in the space over the surface of the reticle, a light absorbing member extending in the scanning direction of the light beam is disposed in the direction in which scattered light (stray light) appearing from the surface or end surface of the reticle is created, and a light intercepting member is disposed in such a direction which does not intercept the optical path of the light beam and the optical path along which the scattered light from the foreign particle arrives at the light receiving element. This light intercepting member has intercepted stray light resulting from part of the laser light which enters the reticle being repetitively reflected within the reticle and travelling away from the laser source and being reflected by an end surface of the reticle. The erroneous detection by the foreign particle inspection apparatus caused by stray light has been reduced by this light intercepting member.

However, even the use of the prior-art light intercepting member could not completely intercept stray light.

SUMMARY OF THE INVENTION

It is an object of the present invention to provide a foreign particle inspection apparatus in which erroneous detection is prevented.

The inventors, as the result of their ardent studies, have made it clear that stray light which could not be intercepted by the prior-art light intercepting member is created from the end surface of a reticle which is closer to a light source than to the incidence position of a light beam. This stray light which cannot be intercepted in the prior-art apparatus will now be described. A factor for the creation of the stray light is diffracted light from a circuit pattern. As the circuit pattern becomes minute, the angle of diffraction of diffracted light which is created from the circuit pattern and enters into the reticle becomes greater and this diffracted light is repetitively reflected in the reticle and travels toward a laser source. Scattered light (stray light) is created from one of the end surfaces of the reticle which is nearer the light source than the scanning area of the laser beam on the reticle, and enters the light receiving surface of a light receiving element and thus, erroneous detection is caused. Another factor for the creation of the stray light is edge scattered light from the circuit pattern. This scattered light is repetitively reflected in the reticle and travels toward the laser source, and creates stray light from the end surface of the reticle which is nearer the light source than the scanning area.

The scattered and diffracted lights from the circuit pattern which is created when light is applied to the reticle is, for example, as shown in FIG. 5 of the accompanying drawings. Here, by the incident light beam being applied to the reticle, pattern scattered light or diffracted light A-E is created. These pattern scattered light or diffracted light E enters, for example, the light receiving surface 100a of one of a plurality of light receiving devices, 100, but this pattern scattered light or diffracted light E does not enter the other light receiving devices because it has high directionality. Consequently, it can be discriminated from foreign particle scattered light by finding the logical product of the signals of the plurality of light receiving devices. That is, only when the scattered light enters all of the plurality of light receiving devices, it is detected as foreign particle scattered light. However, the pattern scattered light or diffracted lights C and D which enters the reticle 101 is partly reflected (multiplexly reflected) and propagated in the reticle 101 and arrives at the end surface 101a of the reticle. Since the end surface 101a of the reticle is usually subjected to a ground glass treatment, the pattern scattered light or diffracted light C and D which has arrived at the end surface 101a emerges as scattered light (stray light) 102. This stray light 102 is low in directionality and therefore enters the pluality of light receiving devices, and there occurs the inconvenience that it is erroneously detected as foreign particle scattered light of low directionality.

The present invention provides a foreign particle inspection apparatus in which a light intercepting member is provided on an end surface of an object to be inspected such as a reticle which differs from the surface thereof to be inspected, in order to intercept such stray light.

The light intercepting member of the present invention is provided at a location opposed to an end surface of the object to be inspected, whereby stray light that would be transmitted through the end surface of the object can be intercepted.

The light intercepting member of the present invention intercepts scattered light or diffracted light from a circuit pattern on the object to be inspected which is propagated in the object to be inspected and that would be transmitted through the end surface.

The light receiving member of the present invention moves with a stage member.

By the provision of such a light intercepting member, the aforementioned erroneous detection based on the scattered light from an end surface of the object to be inspected can be prevented over the whole surface of the reticle. Also, it becomes possible to make the slice level in U.S. Pat. No. 4,468,120 small and accordingly, to enhance the detection sensitivity to foreign particles. Some embodiments of the present invention will hereinafter be described with reference to the accompanying drawings.

DETAILED DESCRIPTION OF THE PREFERRED EMBODIMENT

Figure 1:
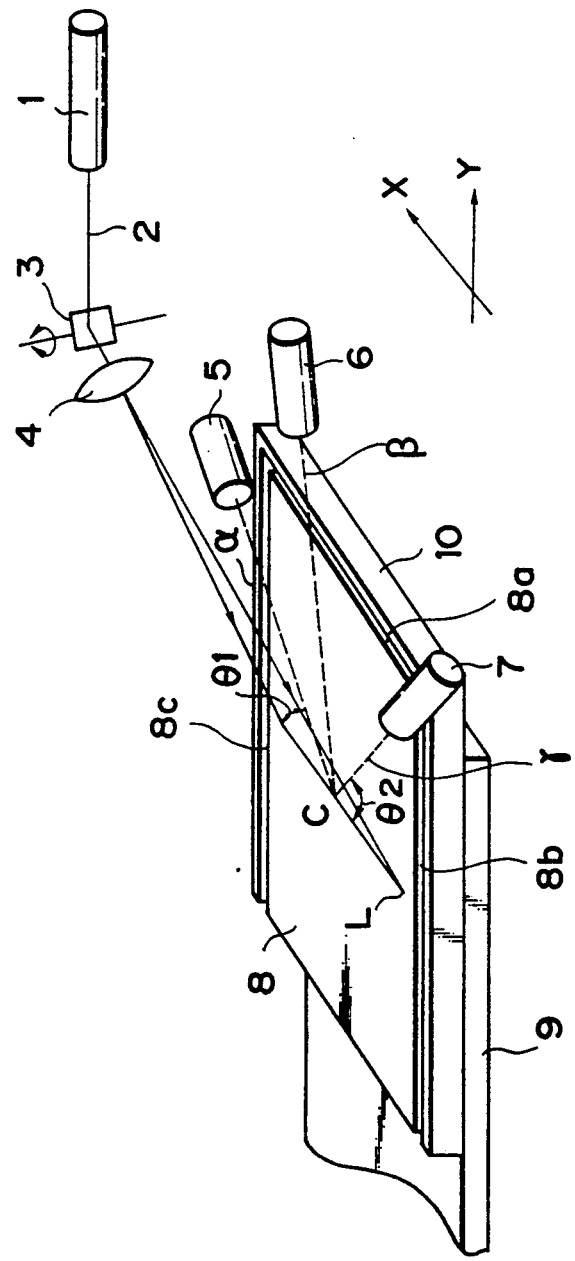
FIG. 1 schematically shows the construction of a foreign particle inspection apparatus according to a first embodiment of the present invention.

FIG. 1 schematically shows the construction of a foreign particle inspection apparatus according to a first embodiment of the present invention. A light beam 2 such as a laser beam emitted from a light source 1 is swept by a vibratory mirror 3 and enters a scanning lens 4. The light source 1 is comprised of a laser source such as He-Ne laser (wavelength 633 nm). The light beam 2 is applied as spotlight L onto the surface of a reticle 8 by the scanning lens, and scans any given range in the direction of the X-axis (scanning direction). The reticle 8 is placed on a stage 9 movable in the direction of the Y-axis, and the scanning of the whole surface of the reticle 8 is possible by the scanning of the spotlight L in the direction of the X-axis and the movement of the stage 9 in the direction of the Y-axis. A minute circuit pattern is formed on the surface of the reticle 8, and when the light beam 2 is applied to this circuit pattern, scattered light or diffracted light is created from the circuit pattern.

Light receiving devices 5, 6 and 7 are disposed in the space above the upper surface of the reticle 8 in such a manner that the centers thereof are directed toward the center C of the scanning range. The light receiving devices 5, 6 and 7 are disposed adjacent to the scanning lens 4 side in such a manner that segments $\alpha$, $\beta$ and $\gamma$ linking the centers of the light receiving devices 5, 6 and 7 to the center C of the scanning range intersect the upper surface of the reticle 8 (that surface opposite to the stage 9 side) at a small angle (of the order of 2°-30°). Also, the light receiving devices 5 and 7 are disposed so that the azimuth angles $\theta 1$ and $\theta 2$ of the segments $\alpha$ and $\gamma$ linking the centers of the light receiving devices 5 and 7 to the center C of the scanning range with respect to the X-axis may be about 15°-80°, and the light receiving device 6 is disposed between the light receiving device 5 and the light receiving device 7. The logical product of electrical signals from these light receiving devices which conform to the intensities of the received light is found by discrimination means (a logic circuit), not shown, whereby the presence or absence of any foreign particle is detected.

Figure 2:
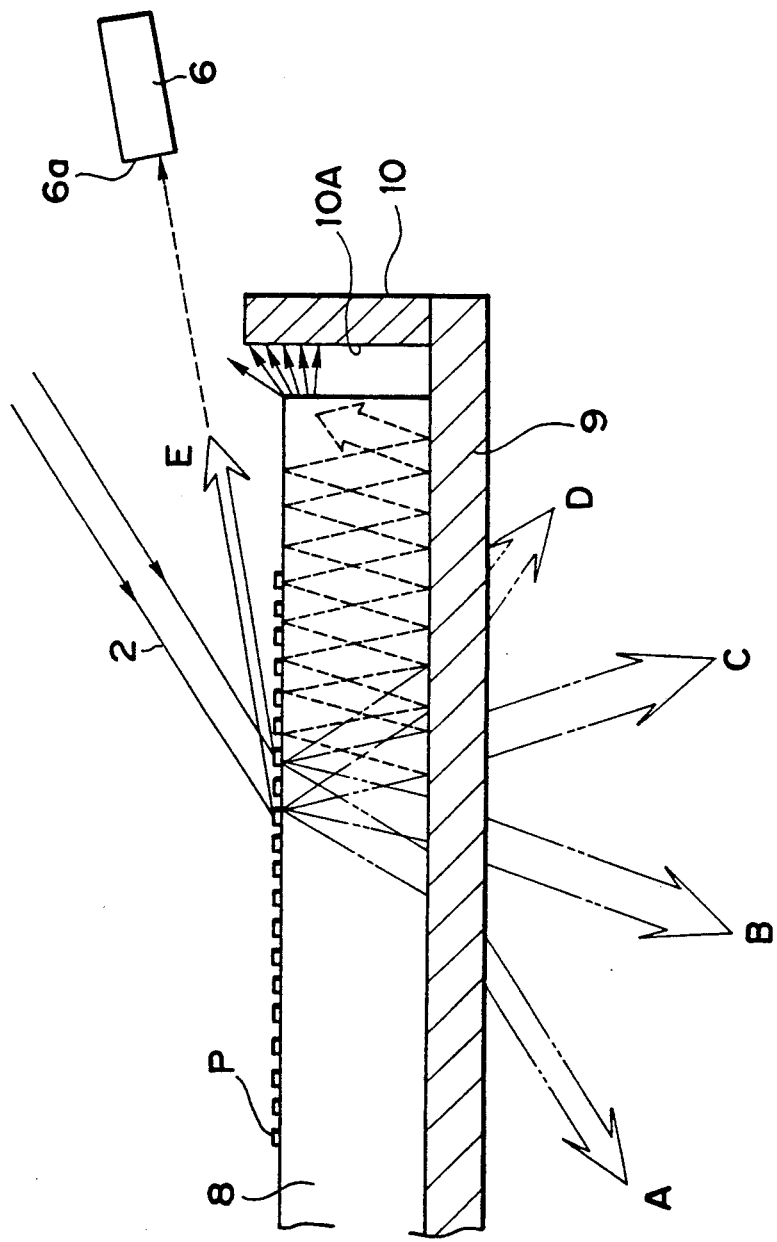
FIG. 2 is a fragmentary cross-sectional view of the apparatus of FIG. 1.

A light intercepting frame 10 is secured onto the stage 9 so as to cover the end surfaces 8a, 8b and 8c of the reticle 8. FIG. 2 is a cross-sectional view of the marginal portion of the reticle in the apparatus of FIG. 1. As shown in FIG. 2, the height of the light intercepting frame 10 is substantially equal to or somewhat greater than that of the surface of the reticle 8. Also, the surface 10A of the light intercepting frame 10 which is opposed to the end surface 8a of the reticle is subjected to a treatment such as the provision of anti-reflection film endowed with an absorbing property capable of sufficiently absorbing the wavelength of the light beam 2, in order to prevent scattered light or diffracted light from the circuit pattern which has entered the reticle from being propagated in the reticle to thereby permit stray light emerging from the end surface 8a of the reticle to enter into the reticle 8 again. There is a slight clearance between the surface 10A of the light intercepting frame 10 and the end surface 8a of the reticle 8, thereby preventing the creation of dust caused by the contact of the light intercepting frame 10 with the reticle 8 when the reticle 8 is placed.

Likewise, anti-reflection film is provided on the surface 10A of the light intercepting frame 10 which is opposed to the end surfaces 8b and 8c, and there is provided a slight clearance between the end surfaces 8b, 8c and the surface 10A of the light intercepting frame 10. This light intercepting frame 10 need not cover the entire periphery of the reticle 8, but sufficiently may cover the end surface in the direction in which the light receiving devices 5, 6 and 7 look at the reticle 8 (the direction in which the light receiving devices are opposed to the reticle), and can effectively intercept the stray light if it covers one of the end surfaces of the reticle which lies on the light source side from the scanning range of the light beam 2 on the reticle 8. The light receiving device 5 is opposed to the end surface 8c or both of the end surfaces 8c and 8a, the light receiving device 6 is opposed to the end surface 8a, and the light receiving device 7 is opposed to the end surface 8b or both of the end surfaces 8b and 8a.

The light intercepting frame 10 moves with the stage 9 and can therefore intercept the stray light irrespective of the positions of the stage 9 and the light receiving devices.

Figure 3:
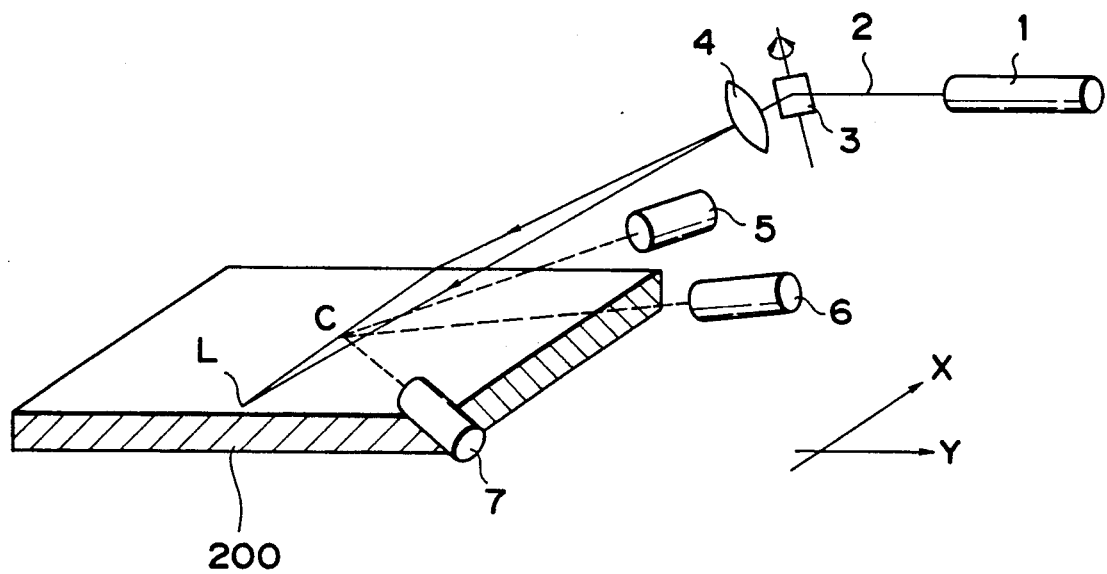
FIG. 3 schematically shows the construction of a foreign particle inspection apparatus according to a second embodiment of the present invention.
Figure 4:
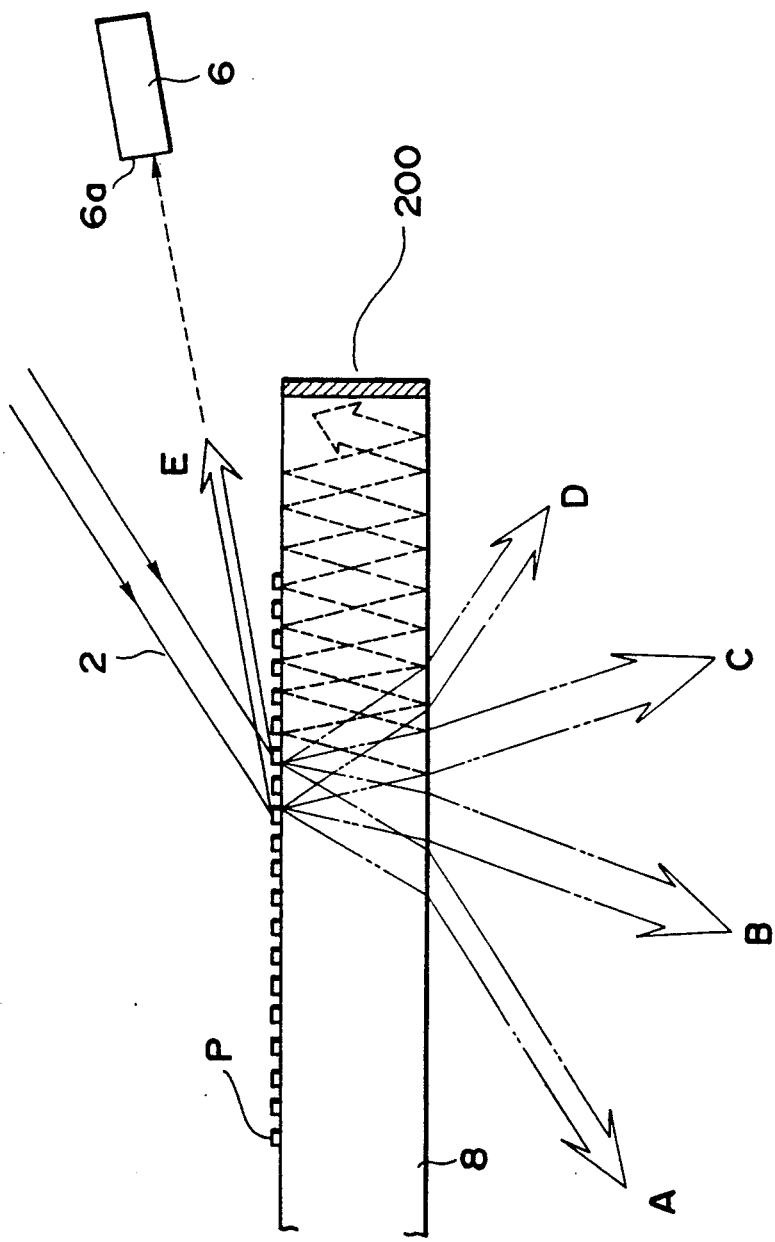
FIG. 4 is a fragmentary cross-sectional view of the apparatus of FIG. 3.
Figure 5:
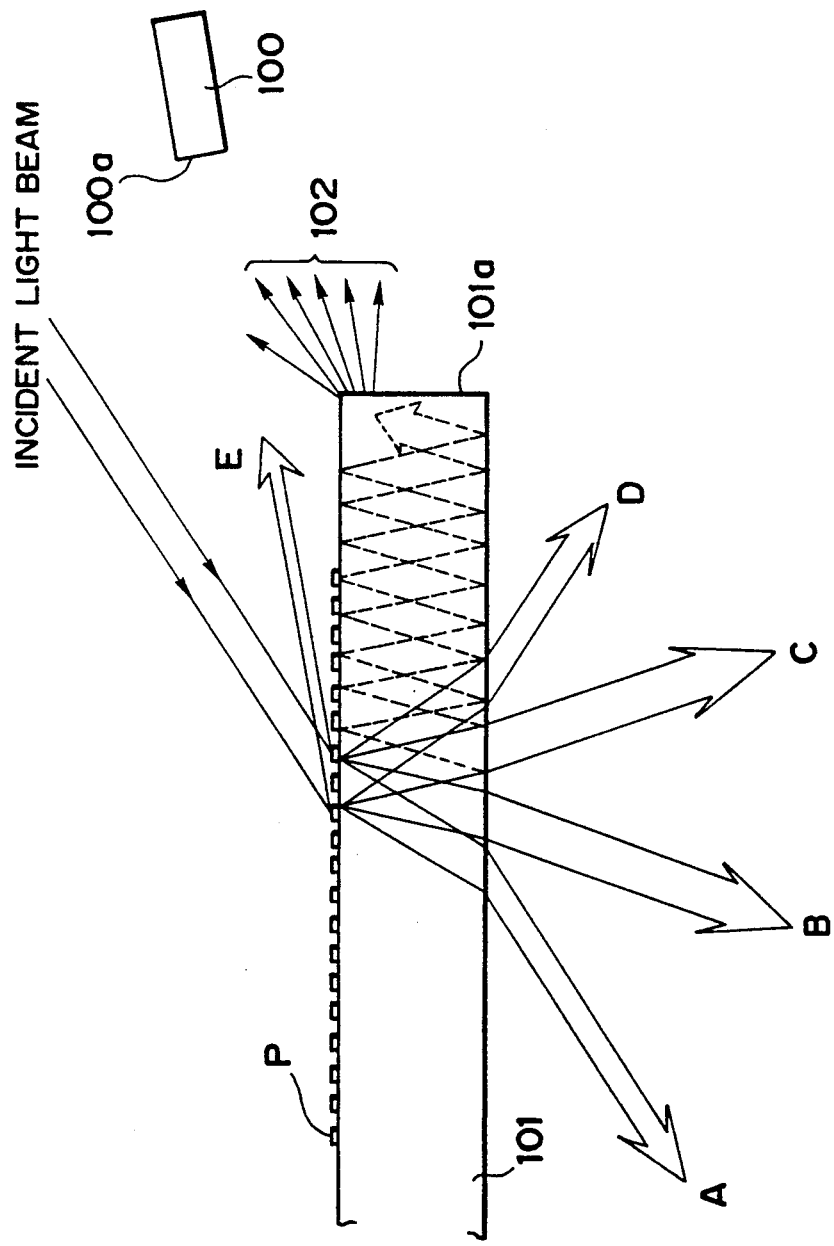
FIG. 5 shows the manner in which pattern scattered light or diffracted lights and stray light are created when light is applied to a reticle.

A second embodiment of the present invention will now be described with reference to FIGS. 3 and 4. FIG. 3 schematically shows the construction of a foreign particle inspection apparatus according to the present embodiment, and FIG. 4 is a cross-sectional view of the apparatus of FIG. 3. In these figures, members similar to those in FIG. 1 are given similar reference numerals, and the stage 9 is omitted.

In the first embodiment, the light intercepting frame 10 is provided as light intercepting means for preventing the stray light, whereas in the present embodiment, light intercepting film 200 endowed with a characteristic capable of sufficiently absorbing the wavelength of the light beam 2 is provided on that end surface of the reticle 8 which is opposed to the light receiving devices. Thereby, the creation of stray light entering the light receiving devices can be prevented as shown in FIG. 4. The light intercepting film 200 may be applied to the end surface of the reticle 8, or may be stuck to or deposited by evaporation on the end surface of the reticle 8.

In the above-described embodiments, the light receiving devices are disposed in the space above the upper surface of the reticle 8, but the stray light can be effectively prevented by the aforedescribed light intercepting means even if the light receiving devices are disposed in the space below the underside of the reticle 8 (the surface which is adjacent to the stage 9).

We claim:

1. A foreign particle inspection apparatus for detecting any foreign particle present on a transparent object to be inspected, comprising:
    applying means having a light source obliquely emitting a light beam onto one surface of said object;
    moving means for moving said object and said light beam relative to each other for the scanning of an area of said surface by said light beam;
    a photoelectric converter having a light receiving surface disposed to oppose said surface of said object and at least one end of said object, said photoelectric converter receiving scattered light from said foreign particle incident on said light receiving surface and outputting an electrical signal conforming to the intensity of the received light; and
    a light intercepting member disposed for intercepting light propagated in said object from said scanning area toward said end of said object, that would otherwise be transmitted through said end and travel externally of said object to said light receiving surface.

2. A foreign particle inspection apparatus according to claim 1, wherein said moving means has a stage member for moving said object to be inspected relative to said applying means, and said light intercepting member moves with said stage member.

3. A foreign particle inspection apparatus according to claim 1, wherein said light intercepting member is disposed in opposed relationship with and with a predetermined spacing with respect to said end of said object.

4. A foreign particle inspection apparatus according to claim 3, wherein said light intercepting member has a wall surface substantially parallel to said end.

5. A foreign particle inspection apparatus according to claim 4, wherein said wall surface has an upper end portion protruding beyond said surface of side object.

6. A foreign particle inspection apparatus according to claim 4, wherein said wall surface has anti-reflection film opposed to said end.

7. A foreign particle inspection apparatus according to claim 1, wherein said light intercepting member includes a light intercepting frame surrounding said end.

8. A foreign particle inspection apparatus according to claim 7, wherein said object to be inspected is of a planar shape having a predetermined thickness, and the height of said light intercepting frame in the direction of said thickness is equal to or greater than the thickness of said object to be inspected.

9. A foreign particle inspection apparatus according to claim 1, wherein said light intercepting member includes light intercepting film applied to said end of said object.

10. A foreign particle inspection apparatus for detecting any foreign particle present on a transparent object to be inspected having a minute pattern thereon, comprising:
    applying means having a light source obliquely emitting a light beam onto one surface of said object;
    moving means for moving said object to be inspected and said light beam relative to each other for the scanning of an area of said surface by said light beam;
    a photoelectric converter having a light receiving surface disposed to oppose said surface of said object and at least one end of said object, said photoelectric converter receiving scattered light from said foreign particle incident on said light receiving surface and outputting an electrical signal conforming to the intensity of the received light; and
    a light intercepting member disposed for receiving at least one of light scattered by and light diffracted by said pattern at said scanning area, and intercepting light propagated in said object from said scanning area toward said end of said object, that would otherwise by transmitted through said end and travel externally of said object to said light receiving surface.

11. A foreign particle inspection apparatus according to claim 1, wherein said scanning area is disposed between said end of said object and an opposite end of said object, and wherein the distance between the first-mentioned end and said light source is less than the distance between said opposite end and said light source.

* * * * *